(12) United States Patent
Haque et al.

(10) Patent No.: US 10,402,928 B2
(45) Date of Patent: Sep. 3, 2019

(54) FLEXIBLE CARE PLAN METHODS AND APPARATUSES

(71) Applicant: KONINKLIJKE PHILIPS N.V., Eindhoven (NL)

(72) Inventors: Imtiyaz Haque, Cupertino, CA (US); Yaqiong Fang, Milpitas, CA (US); Brian Zhou, San Jose, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 596 days.

(21) Appl. No.: 14/681,148

(22) Filed: Apr. 8, 2015

(65) Prior Publication Data
US 2015/0213200 A1 Jul. 30, 2015

Related U.S. Application Data

(62) Division of application No. 12/096,040, filed as application No. PCT/IB2006/054609 on Dec. 5, 2006.
(Continued)

(51) Int. Cl.
*G16H 80/00* (2018.01)
*G06Q 50/24* (2012.01)
(Continued)

(52) U.S. Cl.
CPC .......... *G06Q 50/24* (2013.01); *G06F 19/325* (2013.01); *G06F 19/3418* (2013.01);
(Continued)

(58) Field of Classification Search
CPC ............ G06F 13/1605; G06F 19/327; G06F 17/30867; G06F 17/3089; G06Q 10/06;
(Continued)

(56) References Cited

U.S. PATENT DOCUMENTS 5,721,829 A    2/1998   Dunn et al.
5,864,684 A *   1/1999   Nielsen ................ G06Q 10/107
                                                    709/206
(Continued)

FOREIGN PATENT DOCUMENTS

DE    10125504 A1   12/2005
EP    1443444 A2   8/2004
(Continued)

OTHER PUBLICATIONS

Kramer et al, "Task Swapping for Schedule Improvement: A Broader Analysis", Proc. 14th International Conference on Automated Planning and Scheduling, Jun. 2004, 9 Pages.
(Continued)

*Primary Examiner* — John A Pauls

(57) ABSTRACT

A care plan management system (10) includes storage (16) containing (i) care management-related content (14) and (ii) a patient care plan (21, 22, 23) including at least a schedule for presenting selected care management-related content. A user interface (31, 32, 33) is configured to receive and present care management-related content. At least one processor (26, 44) communicates with the storage and the user interface. The at least one processor is configured to communicate care management-related content to the user interface in accordance with the patient care plan and to automatically adjust the schedule of the patient care plan to free up a selected time period (54).

14 Claims, 16 Drawing Sheets

Related U.S. Application Data

(60) Provisional application No. 60/742,293, filed on Dec. 5, 2005.

(51) Int. Cl.
  *G06F 19/00* (2018.01)
  *G06Q 50/22* (2018.01)
  *G16H 10/60* (2018.01)
  *G16H 50/20* (2018.01)

(52) U.S. Cl.
  CPC ......... *G06F 19/3481* (2013.01); *G06Q 50/22* (2013.01); *G16H 10/60* (2018.01); *G16H 50/20* (2018.01)

(58) Field of Classification Search
  CPC .......... G06Q 10/109; G09B 5/00; G09B 7/00; G09B 7/02; G16H 80/00
  See application file for complete search history.

(56) References Cited

U.S. PATENT DOCUMENTS

| | | | |
|---|---|---|---|
| 7,020,893 | B2 | 3/2006 | Connelly |
| 7,096,271 | B1 | 8/2006 | Omoigui et al. |
| 2002/0018241 | A1* | 2/2002 | Brewster ........... G06F 17/30867 358/402 |
| 2002/0046062 | A1 | 4/2002 | Kameda |
| 2002/0046202 | A1* | 4/2002 | Honda ..................... G09B 7/00 |
| 2002/0055089 | A1* | 5/2002 | Scheirer ................... G09B 7/02 434/350 |
| 2002/0165898 | A1* | 11/2002 | Duffy ................. G06F 13/1605 718/102 |
| 2002/0186243 | A1 | 12/2002 | Ellis et al. |
| 2003/0014491 | A1* | 1/2003 | Horvitz ................ G06Q 10/109 709/206 |
| 2003/0050801 | A1 | 3/2003 | Ries et al. |
| 2004/0034288 | A1* | 2/2004 | Hennessy ............ A61B 5/7435 600/300 |
| 2004/0117459 | A1* | 6/2004 | Fry ..................... H04M 3/5307 709/219 |
| 2004/0249672 | A1 | 12/2004 | Bocionek et al. |
| 2005/0086082 | A1 | 4/2005 | Braunstein et al. |
| 2005/0114178 | A1 | 5/2005 | Krishnamurthy et al. |
| 2005/0233290 | A1 | 10/2005 | Jackson |
| 2005/0235060 | A1 | 10/2005 | Brown |
| 2005/0288987 | A1 | 12/2005 | Sattler et al. |
| 2006/0143060 | A1* | 6/2006 | Conry ................... G06F 19/327 705/7.19 |
| 2006/0173723 | A1* | 8/2006 | Fisher .................... G06Q 10/06 705/7.24 |
| 2007/0099161 | A1* | 5/2007 | Krebs ...................... G09B 5/00 434/322 |
| 2007/0100829 | A1* | 5/2007 | Allen .................. G06F 17/3089 |

FOREIGN PATENT DOCUMENTS

| | | |
|---|---|---|
| WO | 9715022 A1 | 4/1997 |
| WO | 0176226 A2 | 10/2001 |
| WO | 2006006969 A1 | 1/2005 |
| WO | WO-2007020601 A2 * | 2/2007 ........... G06F 19/327 |

OTHER PUBLICATIONS

Guillen, "Multimedia Telehomecare System Using Standard TV Set", IEEE Transactions on Biomedical Engineerg, vol. 49, No. 12, Dec. 2002, p. 1431-1437.

* cited by examiner

| Content session | Scheduled time |
|---|---|
| Session #A | Monday, August 7, 2006 |
| Session #B | Tuesday, August 8, 2006 |
| Session #C | Wednesday, August 9, 2006 |
| Session #D | Thursday, August 10, 2006 |
| Session #E | Friday, August 11, 2006 |
| --- | Saturday, August 12, 2006 |
| --- | Sunday, August 13, 2006 |
| Session #F | Monday, August 14, 2006 |
| Session #G | Tuesday, August 15, 2006 |
| Session #H | Wednesday, August 16, 2006 |

Sessions #C, #D, #E: Vacation (54)

System clock = Tuesday, August 8, 2006 10:06 p.m.

Fig. 2

| Content session | Scheduled time |
|---|---|
| Session #A | Monday, August 7, 2006 |
| Session #B | Tuesday, August 8, 2006 |
| N/A | Wednesday, August 9, 2006 |
| N/A | Thursday, August 10, 2006 |
| N/A | Friday, August 11, 2006 |
| --- | Saturday, August 12, 2006 |
| --- | Sunday, August 13, 2006 |
| Session #C | Monday, August 14, 2006 |
| Session #D | Tuesday, August 15, 2006 |
| Session #E | Wednesday, August 16, 2006 |
| Session #F | Thursday, August 17, 2006 |
| Session #G | Friday, August 18, 2006 |
| --- | Saturday, August 19, 2006 |
| --- | Sunday, August 20, 2006 |
| Session #H | Monday, August 21, 2006 |

System clock = Tuesday, August 8, 2006

Fig. 3

| Content session | Scheduled time |
|---|---|
| Session #1 | Monday, August 7, 2006 |
| Session #2 | Tuesday, August 8, 2006 |
| Session #3 | Wednesday, August 9, 2006 |
| Session #4 | Thursday, August 10, 2006 |
| Session #5 | Friday, August 11, 2006 |
| Session #6 | Saturday, August 12, 2006 |
| Session #7 | Sunday, August 13, 2006 |
| Session #8 | Monday, August 14, 2006 |
| Session #9 | Tuesday, August 15, 2006 |
| Session #10 | Wednesday, August 16, 2006 |

Sessions #3–#5: Vacation

System clock = Tuesday, August 8, 2006

Fig. 4

| Content session | Scheduled time |
|---|---|
| Session #1 | Monday, August 7, 2006 |
| Session #2 | Tuesday, August 8, 2006 |
| N/A | Wednesday, August 9, 2006 |
| N/A | Thursday, August 10, 2006 |
| N/A | Friday, August 11, 2006 |
| Session #3 | Saturday, August 12, 2006 |
| Session #4 | Sunday, August 13, 2006 |
| Session #5 | Monday, August 14, 2006 |
| Session #6 | Tuesday, August 15, 2006 |
| Session #7 | Wednesday, August 16, 2006 |
| Session #8 | Thursday, August 17, 2006 |
| Session #9 | Friday, August 18, 2006 |
| Session #10 | Saturday, August 19, 2006 |

56'

54 } Vacation

System clock = Tuesday, August 8, 2006 — 50

Fig. 5

| Content session | Scheduled time |
|---|---|
| Session #1 | Monday, August 7, 2006 |
| Session #2 | Tuesday, August 8, 2006 |
| N/A | Wednesday, August 9, 2006 |
| N/A | Thursday, August 10, 2006 |
| N/A | Friday, August 11, 2006 |
| Session #3<br>Session #4 | Saturday, August 12, 2006 |
| Session #5 | Sunday, August 13, 2006 |
| Session #6<br>Session #7 | Monday, August 14, 2006 |
| Session #8 | Tuesday, August 15, 2006 |
| Session #9<br>Session #10 | Wednesday, August 16, 2006 |

Rows for Aug 9–11 bracketed as "Vacation" (54). Table labeled 80.

System clock = Tuesday, August 8, 2006 — 50

Fig. 9

| Content session | Scheduled time |
|---|---|
| Session #1 | Monday, August 7, 2006 |
| Session #2 Session #3 | Tuesday, August 8, 2006 |
| N/A | Wednesday, August 9, 2006 |
| N/A | Thursday, August 10, 2006 |
| N/A | Friday, August 11, 2006 |
| Session #4 | Saturday, August 12, 2006 |
| Session #5 Session #6 | Sunday, August 13, 2006 |
| Session #7 | Monday, August 14, 2006 |
| Session #8 Session #9 | Tuesday, August 15, 2006 |
| Session #10 | Wednesday, August 16, 2006 |

Vacation (rows Wednesday, August 9 – Friday, August 11, 2006)

System clock = Tuesday, August 8, 2006

Fig. 11

| Content session | Scheduled time |
| --- | --- |
| Session #1 | Monday, August 7, 2006 |
| Session #2 | Tuesday, August 8, 2006 |
| N/A | Wednesday, August 9, 2006 |
| N/A | Thursday, August 10, 2006 |
| N/A | Friday, August 11, 2006 |
| Session #6' | Saturday, August 12, 2006 |
| Session #7' | Sunday, August 13, 2006 |
| Session #8' | Monday, August 14, 2006 |
| Session #9 | Tuesday, August 15, 2006 |
| Session #10 | Wednesday, August 16, 2006 |

Vacation (rows for Aug 9–11, 2006)

System clock = Tuesday, August 8, 2006

Fig. 12

| Content session | Scheduled time |
|---|---|
| Session #1 | Monday, August 7, 2006 |
| Session #2 | Tuesday, August 8, 2006 |
| N/A | Wednesday, August 9, 2006 |
| N/A | Thursday, August 10, 2006 |
| N/A | Friday, August 11, 2006 |
| Session #2 | Saturday, August 12, 2006 |
| Session #3 | Sunday, August 13, 2006 |
| Session #4 | Monday, August 14, 2006 |
| Session #5 | Tuesday, August 15, 2006 |
| Session #6 | Wednesday, August 16, 2006 |

Vacation (Wednesday, August 9 – Friday, August 11, 2006)

System clock = Tuesday, August 8, 2006

Fig. 13

| Content session | Scheduled time |
|---|---|
| Session #1 | Monday, August 7, 2006 |
| Session #2 | Tuesday, August 8, 2006 |
| N/A | Wednesday, August 9, 2006 |
| N/A | Thursday, August 10, 2006 |
| N/A | Friday, August 11, 2006 |
| Session #HS (health survey) Session #3 | Saturday, August 12, 2006 |
| Session #4 | Sunday, August 13, 2006 |
| Session #5 | Monday, August 14, 2006 |
| Session #6 | Tuesday, August 15, 2006 |
| Session #7 | Wednesday, August 16, 2006 |

System clock = Tuesday, August 8, 2006

Fig. 14

| Goal module #1 (56) | Goal module #2 (130) | Scheduled time |
|---|---|---|
| Session #1 | Session #A | Monday, August 7, 2006 |
| Session #2 | Session #B | Tuesday, August 8, 2006 |
| Session #3 | Session #C | Wednesday, August 9, 2006 |
| Session #4 | Session #D | Thursday, August 10, 2006 |
| Session #5 | Session #E | Friday, August 11, 2006 |
| Session #6 | Session #F | Saturday, August 12, 2006 |
| Session #7 | Session #G | Sunday, August 13, 2006 |
| Session #8 | Session #H | Monday, August 14, 2006 |
| Session #9 |  | Tuesday, August 15, 2006 |
| Session #10 |  | Wednesday, August 16, 2006 |

Vacation — 54 (Wednesday, August 9, 2006 – Friday, August 11, 2006)

System clock = Tuesday, August 8, 2006 — 50

Fig. 15

|                  56'↓         | 130'↓                          |                            |
|-------------------------------|--------------------------------|----------------------------|
| Goal module #1                | Goal module #2                 | Scheduled time             |
| Session #1                    | Session #A                     | Monday, August 7, 2006     |
| Session #2                    | Session #B<br>Session #C       | Tuesday, August 8, 2006    |
| N/A                           | N/A                            | Wednesday, August 9, 2006  |
| N/A                           | N/A                            | Thursday, August 10, 2006  |
| N/A                           | N/A                            | Friday, August 11, 2006    |
| Session #3                    | Session #D<br>Session #E       | Saturday, August 12, 2006  |
| Session #4                    | Session #F                     | Sunday, August 13, 2006    |
| Session #5                    | Session #G<br>Session #H       | Monday, August 14, 2006    |
| Session #6                    |                                | Tuesday, August 15, 2006   |
| Session #7                    |                                | Wednesday, August 16, 2006 |

Vacation ↗54

System clock = Tuesday, August 8, 2006 — 50

Fig. 16

FLEXIBLE CARE PLAN METHODS AND APPARATUSES

This application claims the benefit or priority of and describes relationships between the following applications: wherein this application is a divisional of U.S. patent application Ser. No. 12/096,040, filed Jun. 4, 2008, which is the National Stage of International Application No. PCT/IB2006/054609, filed Dec. 5, 2006, which claims the benefit of U.S. application Ser. No. 60/742,293 filed Dec. 5, 2005, all of which are incorporated herein in whole by reference.

BACKGROUND

The following relates to the health management arts. It finds particular application in conjunction with out-patient management of chronic illnesses such as congestive heart failure, emphysema, chronic obstructive pulmonary disease (COPD), and so forth, and will be described with particular reference thereto. It finds application more generally in conjunction with methods and apparatuses for providing care management for: chronic diseases; rehabilitation from a catastrophic event such as a stroke or an automobile accident; managing weight; controlling insomnia; redressing health-impacting lifestyle issues such as smoking or poor diet or inadequate physical exercise; avoiding potential medical conditions such as osteoporosis or tooth decay; and so forth.

Medical professionals recognize that providing extended-term health care management assistance to chronically ill patients is an important aspect of treating the chronic illness and assuring the patient a high quality of life. Extended term health management is typically performed on an out-patient basis, and is typically wholly or in large part self-administered, perhaps with occasional help from weekly therapy classes or so forth. It is well known, however, that patients often fail to adequately follow the prescribed health care plan outside of a hospital or other supervised setting. This failure can result from lack of understanding of how to perform health care activities, apathy or lack of motivation, fear of failure, or so forth.

Such problems can in principle be overcome by increased one-on-one interaction between the patient and medical personnel. For example, a daily visit to the patient by a traveling nurse could help ensure that the patient is taking medications in a timely fashion and following prescribed dietary and exercise regimens. However, it is often not feasible to provide such intensive one-on-one sessions due to high cost, lack of available medical personnel, or so forth.

In some cases, the patient can choose to access a hospital website or other on-line (e.g., Internet-based) medical database to pull information relevant to the patient's care plan. However, the patient may not have Internet access, or may be unable to navigate a complex on-line medical database. Moreover, providing access to on-line databases does nothing to help patients who are unmotivated. Other approaches that have been used include providing the patient with instructional or motivational videos. However, these approaches do not provide interactive assistance of a type likely to encourage the patient to follow care plan regimens. Moreover, passive videos are difficult to personalize so as to directly address specific issues related to the patient.

Royal Philips Electronics, Cardiovascular Associates of the Delaware Valley, and Comcast Corporation have announced a cooperative effort called Motiva™ to provide a test group of chronic heart failure patients with a remote patient management broadband-enabled platform for connecting the test patients with their healthcare community. The Motiva™ system provides a cable television-based interactive health care management platform, in which content such as educational video, medication scheduling, personalized encouragement and reinforcement, and so forth, is pushed to the patient based on a personalized health care plan. Feedback from the patient, for example through the use of interactive surveys, enables the Motiva™ system to adjust or personalize content to the needs of each patient. The Motiva™ system can deliver personalized health care management assistance to patients on a daily or more frequent basis.

One problem that arises in maintaining such a personalized interactive care management system is time management. Typically, the care plan is organized into content sessions that are presented to the patient on a pre-determined schedule. This approach works well as long as the patient adheres to the schedule. However, the patient may go on vacation, take a work-related trip, or encounter another situation which causes the patient to miss one or more scheduled sessions.

The patient may attempt to "squeeze in" the missed session by accessing several sessions in succession on the same day or over a few days. However, this approach can lead to information overload if the sessions are long or complex, resulting in the patient failing to comprehend important content. Alternatively, the patient may skip a queued session entirely, which may also cause the patient to miss important content. Moreover, in some cases, it may not be enough to access the queued sessions. For example, if the patient goes on a long vacation, it may be appropriate for the patient to review one or more sessions that had been presented before commencement of the vacation, in order to allow the patient to catch up.

The following contemplates improvements that overcome the aforementioned limitations and others.

BRIEF SUMMARY

According to one aspect, a server for a care management system is disclosed, including storage and at least one processor. The storage contains (i) care management-related content for a plurality of content sessions and (ii) a patient care plan associated with a corresponding patient. The patient care plan includes at least a schedule for presenting selected content sessions to the patient. The at least one processor is configured to control communication of content sessions to the patient in accordance with the patient care plan and to automatically adjust the schedule of the patient care plan to free up a selected time period.

According to another aspect, a care plan management system is disclosed. Storage contains (i) care management-related content and (ii) a patient care plan including at least a schedule for presenting selected care management-related content. A user interface is configured to receive and present care management-related content. At least one processor communicates with the storage and the user interface. The at least one processor is configured to communicate care management-related content to the user interface in accordance with the patient care plan and to automatically adjust the schedule of the patient care plan to free up a selected time period.

According to another aspect, a method is disclosed for managing care. A patient care plan is stored, including at least a schedule for presenting selected content to the patient. The selected content is communicated to a patient in accordance with the patient care plan. During the course of said communicating, the schedule of the patient care plan is automatically adjusted to free up a selected time period.

One advantage resides in a well-ordered resumption of a patient care plan after a vacation or other interruption of the plan.

Another advantage resides in ensuring that the patient does not miss information or other content of the patient's care plan due to vacation or other interruption of the plan Another advantage resides in enabling a patient to get back on schedule after a vacation or other interruption of a care plan, while avoiding overloading the patient with content upon resumption of the plan.

Numerous additional advantages and benefits will become apparent to those of ordinary skill in the art upon reading the following detailed description of the preferred embodiments.

BRIEF DESCRIPTION OF THE DRAWINGS

The invention may take form in various components and arrangements of components, and in various process operations and arrangements of process operations. The drawings are only for the purpose of illustrating preferred embodiments and are not to be construed as limiting the invention.

FIG. 2 diagrammatically shows an initial absolute-date schedule of a patient care plan.

FIG. 3 diagrammatically shows a revised absolute-date schedule constructed from the initial absolute-date schedule of FIG. 2 by translation of scheduled presentations of content sessions coinciding with and subsequent to the patient's vacation. The revised schedule frees up the vacation period.

FIG. 4 diagrammatically shows another initial absolute-date schedule of a patient care plan.

FIG. 5 diagrammatically shows a revised absolute-date schedule constructed from the initial absolute-date schedule of FIG. 4 by translation of scheduled presentations of content sessions coinciding with and subsequent to the patient's vacation. The revised schedule frees up the vacation period.

FIG. 9 diagrammatically shows a revised absolute-date schedule constructed from the initial absolute-date schedule of FIG. 4 by translation of scheduled presentations of content sessions coinciding with the patient's vacation, and speeding up the schedule in the time period proximate to but after the vacation. The revised schedule frees up the vacation period.

FIG. 11 diagrammatically shows a revised absolute-date schedule constructed from the initial absolute-date schedule of FIG. 4 by translation of scheduled presentations of content sessions coinciding with the patient's vacation, and speeding up the schedule in the earlier and later time periods proximate to but not coinciding with the vacation. The revised schedule frees up the vacation period.

FIG. 12 diagrammatically shows a revised absolute-date schedule constructed from the initial absolute-date schedule of FIG. 4 by omission of presentation of the content sessions coinciding with the patient's vacation, and by replacing content sessions in the time period proximate to but after the vacation with modified content sessions that include make-up material.

FIG. 13 diagrammatically shows a revised absolute-date schedule constructed from the initial absolute-date schedule of FIG. 4 by translation of scheduled presentations of content sessions coinciding with the patient's vacation, and by addition of a repeat presentation of the content session immediately preceding the vacation. The revised schedule frees up the vacation period and also provides a review of content covered just prior to commencement of the vacation.

FIG. 14 diagrammatically shows a revised absolute-date schedule constructed from the initial absolute-date schedule of FIG. 4 by translation of scheduled presentations of content sessions coinciding with the patient's vacation, and by addition of a new content session providing a health survey of the patient to assess changes in physical condition that may have occurred during the vacation. The revised schedule frees up the vacation period. Presentation of Session #3 and subsequent sessions is contingent upon satisfactory answers to the health survey.

FIG. 15 diagrammatically shows initial absolute-date schedules of a patient care plan that includes two goal modules.

FIG. 16 diagrammatically shows independently revised absolute-date schedules for the two goal modules constructed from the initial absolute-date schedules of FIG. 15. Both revised schedules free up the vacation period.

DETAILED DESCRIPTION OF THE PREFERRED EMBODIMENTS

Figure 1:
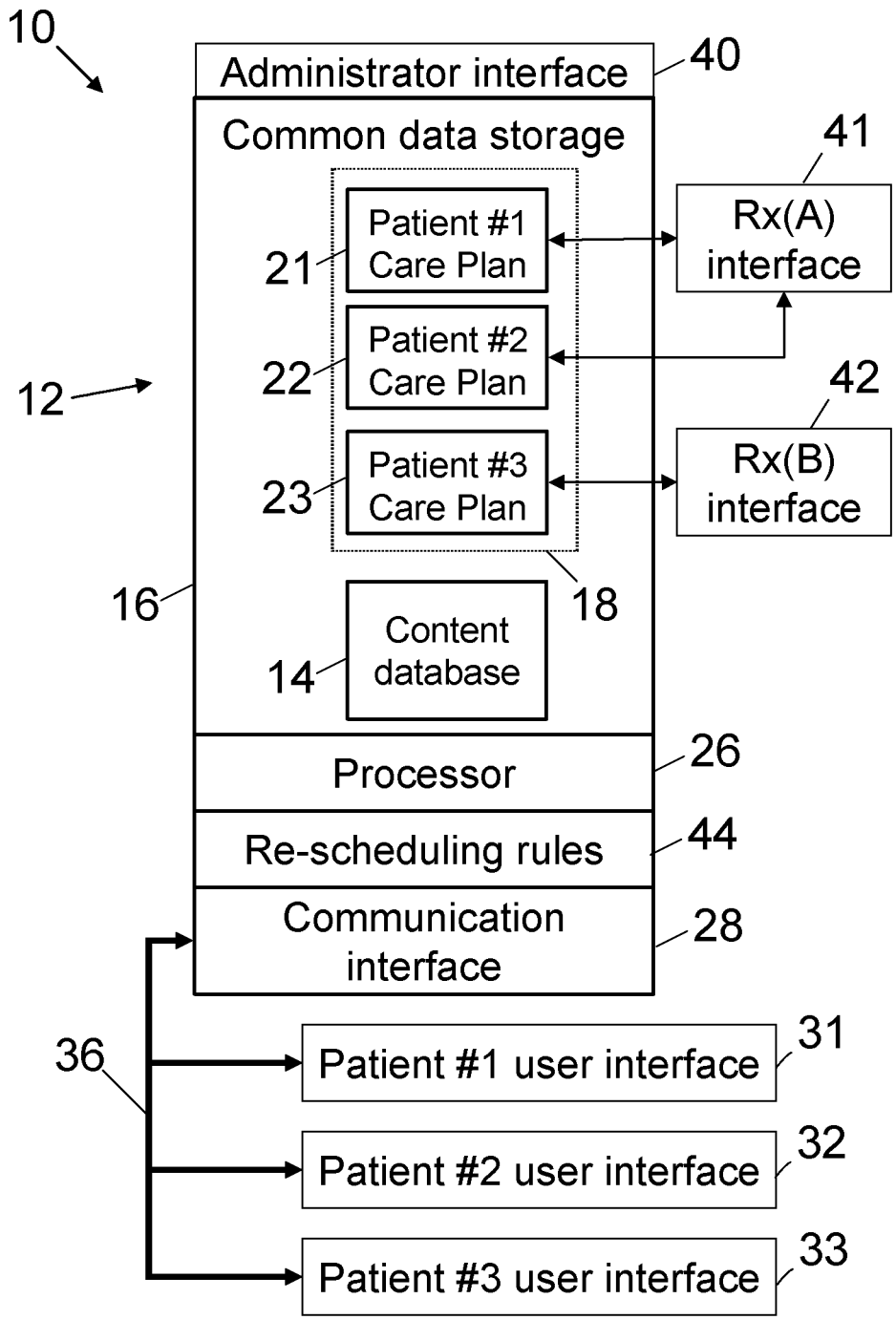
FIG. 1 diagrammatically shows principal components of a personalized interactive care management assistance system.

With reference to FIG. 1, a personalized interactive care management system 10 includes a server 12 for distributing care management-related content. In the example system 10, the content is arranged in a content database 14 stored on storage 16. The server 12 can be embodied in various ways, such as by a centralized computer or computer server, a desktop computer, or so forth. The care management-related content is suitably arranged as content sessions each of which typically includes video content, textual content, surveys, questionnaires, or so forth, or various combinations thereof. For example, content sessions may be provided that are directed toward aspects of reducing weight, stopping smoking, learning to self-administer a medication, learning to use a biometric monitor, learning to follow a dietary restriction such as a low-salt diet, learning to follow a dietary requirement such as a high-fiber diet, performing a physical exercise, or so forth. Optionally, a session may include more than one task or element, such as both audio-video content and a weight measurement acquisition, or patient instruction content followed by an interactive quiz, or so forth.

To enable personalized distributing of content, each patient in the system 10 has an associated care plan that in the illustrated embodiment is stored in a care plans partition 18 of the storage 16. The example storage 16 is logically partitioned to define the content database 14 and the care plan storage 18; however, in other embodiments the storage may include two or more storage elements, which may be different storage media, for storing the care management-related content and the care plan or care plans. In the illustrated embodiment, the storage 16 stores a care plan 21 for Patient #1, a care plan 22 for Patient #2, and a care plan 23 for Patient #3. While only three care plans 21, 22, 23 associated with a corresponding three Patients #1, #2, #3 are illustrated, it is contemplated that the server 12 may store care plans for hundreds or thousands of different patients. As used herein, the term "patient" encompasses persons recovering from surgery, stroke, heart failure, or another condition, persons suffering a chronic illness, or so forth. As used herein, the term "patient" also encompasses other users of the health management system 10 who may be generally healthy but who are following a health management program assisted by the system 10 to maintain fitness, control weight, avoid osteoporosis, or otherwise maintain a healthy condition or make health-related lifestyle modifications.

A processor 26 determines content to be distributed to each patient based on a schedule of the patient care plan of that patient. The processor 26 is configured to control communication of content to the patient in accordance with the patient care plan of that patient. Optionally, rules are applied to determine which content is presented to which patient or patients, the ordering of such content presentation, and so forth. Such rules are optionally used to construct the schedule of each patient care plan. For example, care plan templates may be provided that specify selected content sessions and an order of presentation or linkages between the selected content sessions. Alternatively, the schedule can be constructed more directly, for example by a physician who selects which content sessions to send to his or her patient, and in what order. A communication interface 28 of the server 12 communicates the selected care management-related content to the patient at his or her respective user interface. For example: the communication interface 28 communicates content intended for Patient #1 to a user interface 31 that is accessible by Patient #1; the communication interface 28 communicates content intended for Patient #2 to a user interface 32 that is accessible by Patient #2; the communication interface 28 communicates content intended for Patient #3 to a user interface 33 that is accessible by Patient #3; and so forth.

The user interfaces 31, 32, 33 can employ substantially any hardware capable of providing content presentation and capable of providing feedback to the server 12 via the communication interface 28. For example, the user interfaces 31, 32, 33 can be embodied by hardware such as: a desktop computer; a laptop computer; a personal data assistant (PDA); a cellular telephone (i.e., cellphone); a television set having Internet connectivity integrally included and operated by a television-type remote control or other input device; a digital or analog television set having Internet connectivity provided by an add-on set-top unit and operated by a television remote control, set-top unit remote control, or other input device; or so forth. The communication interface 28 is operatively connected with each of the user interfaces 31, 32, 33 by a pathway or pathways 36 such as the Internet, a cable television network, a satellite television network, a cellular telephone network, or so forth. Moreover, the communication interface 28 optionally includes more than one communication interface. For example, it is contemplated for different user interfaces to connect with the communication interface 28 by different pathways each employing different interface hardware and software. For example, the user interface 31 might be a computer operatively connected with the communication interface 28 by the Internet, while the user interface 32 might be a cellphone connected with the communication interface 28 by a cellular telephone network. To construct such an embodiment, the communication interface 28 suitably includes an Internet port component, and a cellular telephone network port. The pathway or pathways 36 are advantageously secure links because private medical information may be conveyed across the pathway or pathways 36. However, unsecured pathways can also be used. Similarly, each user interface 31, 32, 33 may optionally include more than one user interface. For example, Patient #1 may be able to access the server 12 by his or her computer and also by his or her cellphone. Optionally, the user interface may include one or more biometric feedback monitors each of which measures at least one biometric parameter of an patient that is communicated to the server via the communication interface 28. Suitable biometric monitors may include, for example: a saturated blood oxygen level ($SpO_2$) monitor; a heart rate monitor; a blood pressure monitor; a weight scale; an electrocardiograph (ECG); or so forth. Biometric feedback monitors may be patient-activated—for example, the patient may weigh himself or herself, and then input the weight via the user interface 31, 32, 33. In other embodiments, a patient parameter monitoring session may be included in the schedule, which patient parameter monitoring session leads the patient through the weighing or other biometric monitoring process. In yet other embodiments, a patient parameter monitoring session may be provided which is user-transparent—the session runs concurrently with an instructional session or other session to record patient biometric monitoring data during the instruction.

Maintenance of the server 12 is suitably performed by an administrator via an administrator interface 40. In some embodiments, the administrator interface 40 is suitably a network administrator account having a high level of access to the server 12. The administrator may, for example, add new care management-related content, delete obsolete or outdated care management-related content, organize content, modify or update content flow rules, or so forth. In some embodiments, medical personnel such as doctors or nurses can directly generate and/or update the patient care plans 21, 22, 23 by directly accessing the server 12 via medical personnel interfaces 41, 42. Medical personnel are optionally assigned a lower level of access through a regular user account or other network account providing lower level access limited, for example, to patients of a doctor who is accessing the system 10. For example, the first medical personnel interface 41 accesses the patient care plans 21, 22 of Patients #1 and #2 who are patients of the doctor employing the first medical personnel interface 41, while the second medical personnel interface 42 accesses the patient care plan 23 of Patient #3 who is a patient of the doctor employing the second medical personnel interface 42. In some embodiments, medical personnel interfaces 41, 42 are omitted, and one or more system administrators perform all creation and updating of the patient care plans 21, 22, 23 via the administrator interface 40, and in accordance with instructions from the patient's physician or other medical personnel.

The personalized interactive care management system 10 depicted in FIG. 1 is an example of a relatively centralized system having data storage and computational aspects being disposed at a centralized server 12. Other layouts or system configurations can be employed. For example, the server 12 can be a distributed server embodied by two or more intercommunicating physical computers or other electronic devices communicating via a wired or wireless local area network, the Internet, or another network.

As another example layout or configuration, in some contemplated embodiments copies of the stored data and processing instructions and rules are loaded onto the patient's home computer, laptop computer, PDA, cellphone, or other personal electronic device as a local instance of the management system. The local instance can be loaded onto the patient's computer or other personal electronic device from a compact optical disk (CD) or other portable storage element, or can be loaded by data transmission via the Internet, a cellular telephone network, or so forth. Each patient receives a copy of the system with only his or her own patient care plan included. The patient's home computer embodies the server 12 by executing the local instance of the system, and also embodies the user interface 31, 32, 33. Optionally, the instance disposed on the patient's computer or other personal electronic device communicates survey results, biometric measurements, or other feedback to the hospital, doctor's office, or so forth via the Internet or another network.

With continuing reference to FIG. 1, each patient care plan 21, 22, 23 is constructed with a schedule that is initially determined or presumed to be suitable for the corresponding patient. However, in the course of carrying out the schedule, it may be found that the patient is unavailable, or will be unavailable, during an initially scheduled time for presenting one or more missed content sessions. To enable rescheduling during the course of communicating content in accordance with the schedule, a set of re-scheduling rules 44 configures the processor 26 to automatically adjust the schedule of the patient care plan to free up a patient unavailability time period or other selected time period during which one or more content sessions were originally scheduled. The re-scheduling rules are typically set up by medical personnel when the schedule is constructed or at the time of the re-scheduling; however, it is also contemplated to configure the user interface to enable the patient to set up the re-scheduling rules.

With reference to FIGS. 2 and 3, the first of a number of illustrative examples of applying the re-scheduling rules 44 is set forth. FIG. 2 shows an initial schedule 46, which includes Sessions #A, #B, #C, #D, and #E scheduled for Monday Aug. 7, 2006 through Friday August 11, respectively. The patient is then scheduled to take off the weekend, namely Saturday August 12 and Sunday August 13. Note that this is not an example of patient unavailability, but rather a weekend break intentionally built into the initial schedule 46. Sessions #F, #G, and #H are scheduled for Monday Aug. 14, 2006 through Wednesday August 16, respectively.

The schedule 46 of FIG. 2 employs absolute dates that are applied with reference to a system clock 50. The system clock 50 may, for example, be the system clock of a computer embodying the server 12. In the examples illustrated herein, the schedules for the patient care plans and the system clock 50 each have a temporal granularity of days, which is a typical time increment for a medical care plan. For example, the patient may be expected to view an exercise video every day, take certain medications on a daily basis, or so forth. However, typical digital system clocks have very fine temporal resolution down to the level of a second or smaller time intervals, and accordingly the schedule for the medical care plan can be constructed with a smaller granularity of hours, minutes, or so forth. On the other hand, the schedule can optionally be constructed with a larger granularity such as a week-based granularity.

During the course of presenting content sessions in accordance with the initial schedule 46 of FIG. 2, the patient realizes he or she has a vacation 54 scheduled for three days spanning Wednesday Aug. 9, 2005 through Friday Aug. 11, 2005. Accordingly, the patient provides notice of the planned vacation to the server 12 via his or her respective user interface 31, 32, 33. In response, the processor 26 automatically adjusts the schedule 46 in accordance with the re-scheduling rules 44 to free up the patient unavailability time period corresponding to the vacation 54.

This automatic adjustment of the schedule can be done in various ways. The result of one suitable automatic adjustment is a revised schedule 46' shown in FIG. 3. In the revised schedule 46', the processor 26 has translated the portion of the schedule 46 that was coincident with and subsequent to the patient unavailability or other selected time period 54 forward in time by a selected translation time interval of five days corresponding to the three days of vacation plus the two weekend days. Accordingly, Session C is now scheduled for Monday Aug. 14, 2006, Session D is now scheduled for Tuesday Aug. 15, 2006, Session C is now scheduled for Wednesday Aug. 16, 2006, and so forth. The three vacation days spanning August 9-11 inclusive are suitably labeled as "N/A" indicating that the patient is unavailable, or are left occupied or undesignated on the revised schedule 46'.

With reference to FIGS. 4 and 5, another example is provided of applying the re-scheduling rules 44. FIG. 4 shows an initial schedule 56, which includes Sessions #1-#10 scheduled for Monday Aug. 7, 2006 through Wednesday August 16 inclusive, respectively. Here the patient does not take off the weekend of Saturday August 12 and Sunday August 13. During the course of presenting content sessions in accordance with the initial schedule 56 of FIG. 4, the patient realizes he or she has the vacation 54 scheduled for three days spanning Wednesday Aug. 9, 2005 through Friday Aug. 11, 2005. The patient provides notice of the planned vacation to the server 12 via his or her respective user interface 31, 32, 33. In response, the processor 26 automatically adjusts the schedule 56 in accordance with the re-scheduling rules 44 to free up the patient unavailability time period corresponding to the vacation 54, thus producing the revised schedule 56' shown in FIG. 5. In the revised schedule 56', the processor 26 has operatively translated the portion of the schedule 56 that was coincident with and subsequent to the patient unavailability or other selected time period 54 forward in time by a selected translation time interval of three days corresponding to the three days of vacation. Accordingly, Session #3 is now scheduled for Saturday Aug. 12, 2006, Session #4 is now scheduled for Sunday Aug. 13, 2006, and so forth.

The schedules 46, 46', 56, 56' employ absolute dates that are applied with reference to the system clock 50. However, in some embodiments the schedule does not employ absolute dates, but rather employs relative dates in conjunction with a schedule pointer.

Figure 6:
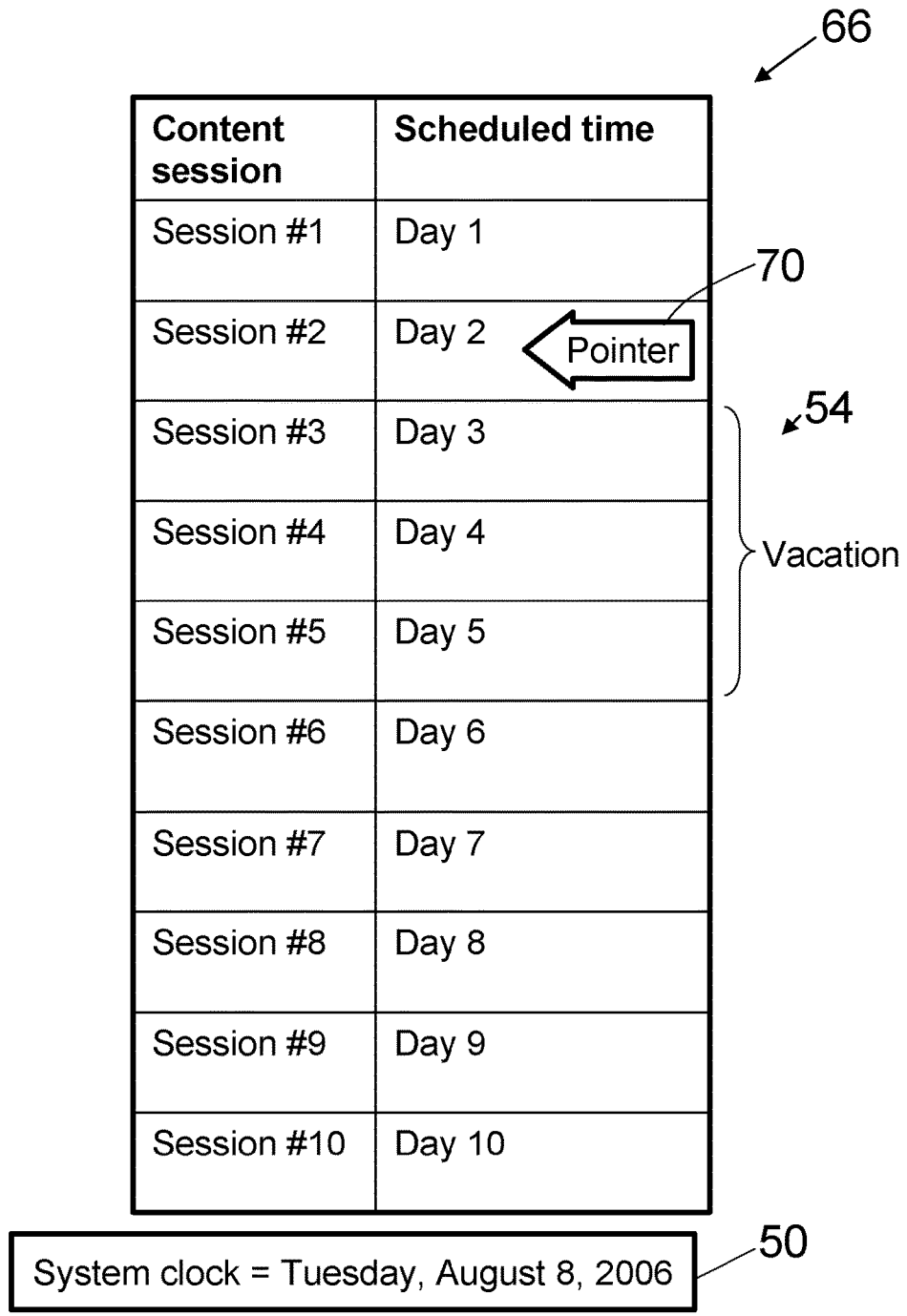
FIG. 6 diagrammatically shows an initial relative-date schedule corresponding to the initial absolute-date schedule of FIG. 4.
Figure 7:
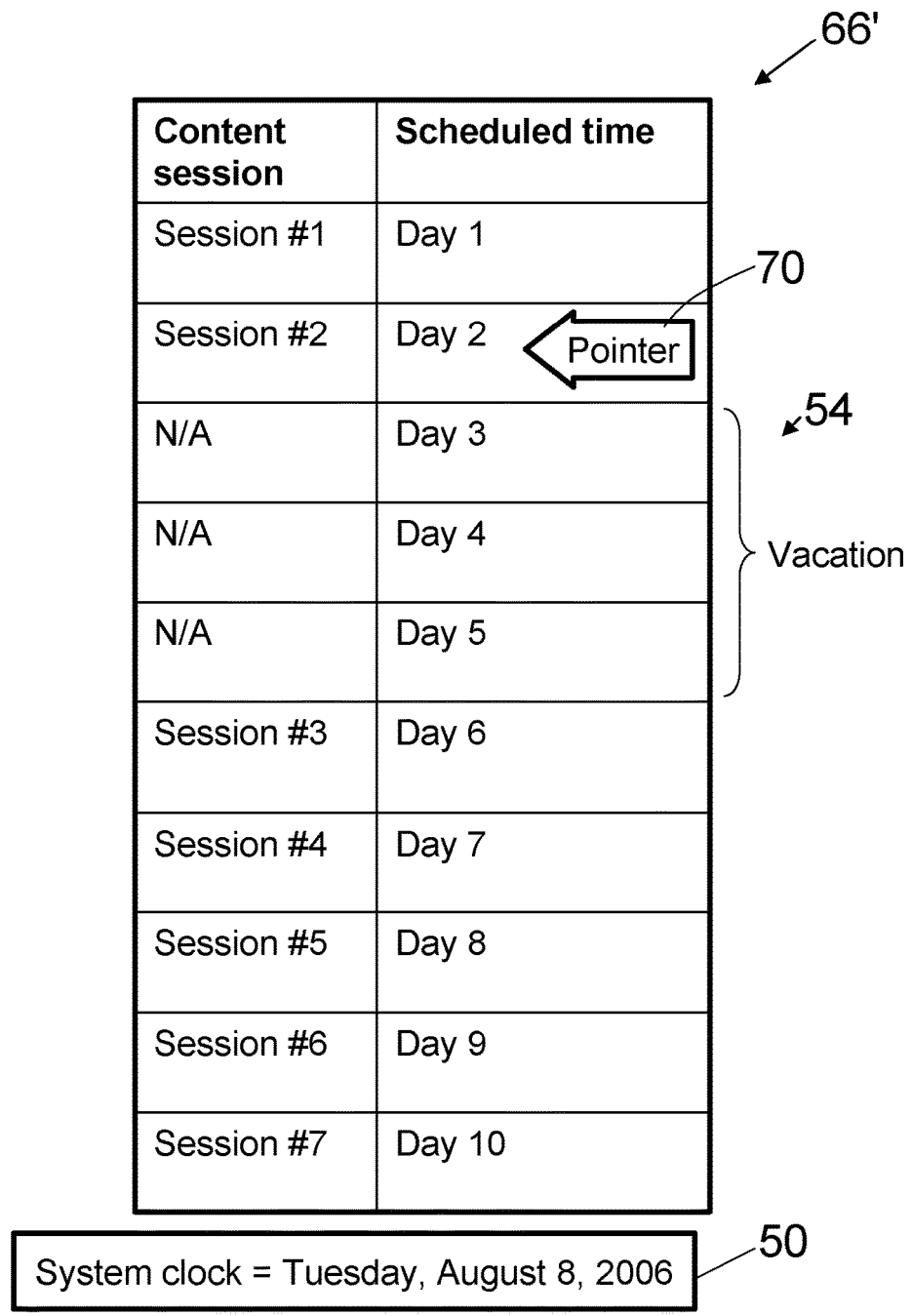
FIG. 7 diagrammatically shows a revised relative-date schedule constructed from the initial relative-date schedule of FIG. 6 by translation of scheduled presentations of content sessions coinciding with and subsequent to the patient's vacation. The revised schedule frees up the vacation period.

With reference to FIGS. 6 and 7, an equivalent of the initial scheduling and rescheduling of FIGS. 4 and 5 is performed using such a relative-date schedule. FIG. 6 shows an initial relative-date schedule 66, which includes the same Sessions #1-#10 as in FIG. 4, identically scheduled for Monday Aug. 7, 2006 through Wednesday August 16 inclusive, respectively. This schedule will be interrupted by the same vacation 54 as in the example of FIG. 4. However, the schedule 56 employs relative dates, so that Session #1 is presented on relative Day 1, Session #2 is presented on relative Day 2, Session #3 is presented on relative Day 3, and so forth. On the date Tuesday Aug. 8, 2006, as indicated by the system clock 50, a schedule pointer 70 points to Day 2, so that Session #2 which is presented on Day 2 is presented on Tuesday Aug. 8, 2006, as indicated by the system clock 50. When the patient realizes he or she has the vacation 54 scheduled for three days spanning Wednesday Aug. 9, 2005 through Friday Aug. 11, 2005, the patient provides notice of the planned vacation to the server 12 via his or her respective user interface 31, 32, 33. In response, the processor 26 automatically adjusts the schedule 66 in accordance with the re-scheduling rules 44 to free up the patient unavailability time period corresponding to the vacation 54, thus producing the revised relative-date schedule 66' shown in FIG. 7. In the revised schedule 66', the processor 26 has operatively translated the portion of the schedule 66 that was coincident with and subsequent to the patient unavailability time period forward in time by a selected translation time interval of three days corresponding to the three days of vacation. Accordingly, Session #3 is now scheduled for relative Day 6 corresponding to Saturday Aug. 12, 2006, Session #4 is now scheduled for relative Day 7 corresponding to Sunday Aug. 13, 2006, Session #5 is now scheduled for relative Day 8 corresponding to Monday Aug. 14, 2006, and so forth. Thus, the re-scheduling from the initial relative-date schedule 66 to the revised relative-date schedule 66' is equivalent to the re-scheduling from the initial absolute-date schedule 56 to the revised absolute-date schedule 56'.

Figure 8:
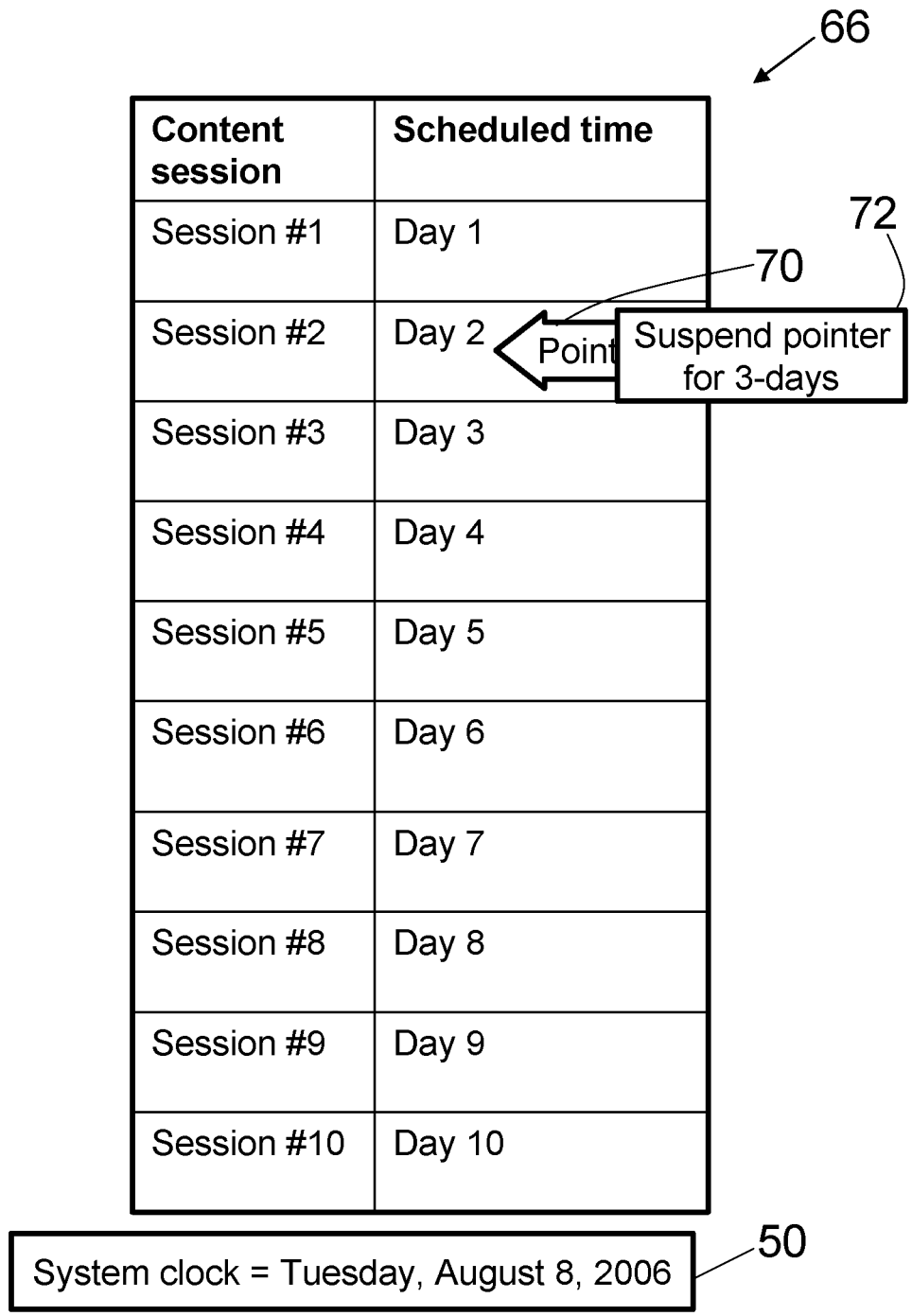
FIG. 8 diagrammatically shows operative adjustment of the initial relative-date schedule of FIG. 6 to free up the vacation by suspending movement of the schedule pointer during the vacation.

With reference to FIG. 8, re-scheduling can also be performed by a different type of automatic adjustment when using a relative-date schedule such as the initial schedule 66. Because the dates are relative, a three-day operative translation of the portion of the schedule coincident with and subsequent to the vacation 54 can be achieved by issuing an instruction 72 to suspend temporal movement of the schedule pointer 70 for the selected three-day translation time interval. In this way, the movement of the schedule pointer 70 from Day 2 to Day 3 will not occur for three days after the present Aug. 8, 2006 date. That is, the movement of the schedule pointer 70 from Day 2 to Day 3 will occur between Friday August 11 and Saturday August 12, so that on Saturday Aug. 12, 2006 the Session #3 will be performed. With movement of the schedule pointer 70 thereafter unsuspended, it follows that Session #4 will be performed on Day 4 now corresponding to Sunday Aug. 13, 2006, Session #5 will be performed on Day 5 now corresponding to Monday Aug. 14, 2006, and so forth.

The revised schedule produced by the automatic adjustment depends upon the choice of rescheduling rules 44 followed by the processor 26 in performing the schedule adjustment. Some further illustrative examples of suitable automatic adjustments of the absolute-date or relative-date initial schedules 56, 66 of FIGS. 4 and 6, respectively, so as to free up the time period of patient unavailability 54 are described with reference to FIGS. 9-14.

With reference to FIG. 9, an alternative revised absolute-date schedule 80 is obtained from the initial absolute-date schedule 56 by applying different selected rescheduling rules 44 that include speeding up the schedule in the time period proximate to but after the patient unavailability time period corresponding to the vacation 54. The revised schedule 80 includes a doubling-up of content sessions on the dates of Saturday Aug. 12, 2006, Monday Aug. 14, 2006, and Wednesday Aug. 16, 2006 which are proximate to but outside of the patient unavailability time period corresponding to the vacation 54. On the first day back from vacation 54, that is, on Saturday Aug. 12, 2006, the patient accesses both Session #3 and Session #4. On the third day back from vacation 54, that is, on Monday Aug. 14, 2006, the patient accesses both Session #6 and Session #7. On the fifth day back from vacation 54, that is, on Wednesday Aug. 16, 2006, the patient accesses both Session #9 and Session #10. Comparison with the initial schedule 56 of FIG. 4 shows that by the end of the fifth day back, the patient is back on schedule. Hence, any future sessions (such as unillustrated Session #11, Session #12, and so forth) are unchanged between the initial schedule 56 and the revised schedule 80. (It will be noted, by contrast, that the revised schedule 56' of FIG. 5 always remains three days behind the initial schedule 56 after the translational three-day revision without speed-up of the schedule.) Construction of the revised schedule 80 also involved adjusting assigned times of content sessions that were previously scheduled proximate to but outside of the patient unavailability time period. Thus, for example, Session #8, which was in the initial schedule 56 assigned for presentation on Monday, Aug. 14, 2006, is in the revised schedule 80 assigned to be presented on Tuesday August 15.

When using relative-time scheduling, a speeded-up schedule can be constructed in the same way as the absolute-time schedule 80 was constructed, that is, by shifting the assigned times of sessions (albeit in relative time) appropriately.

Figure 10:
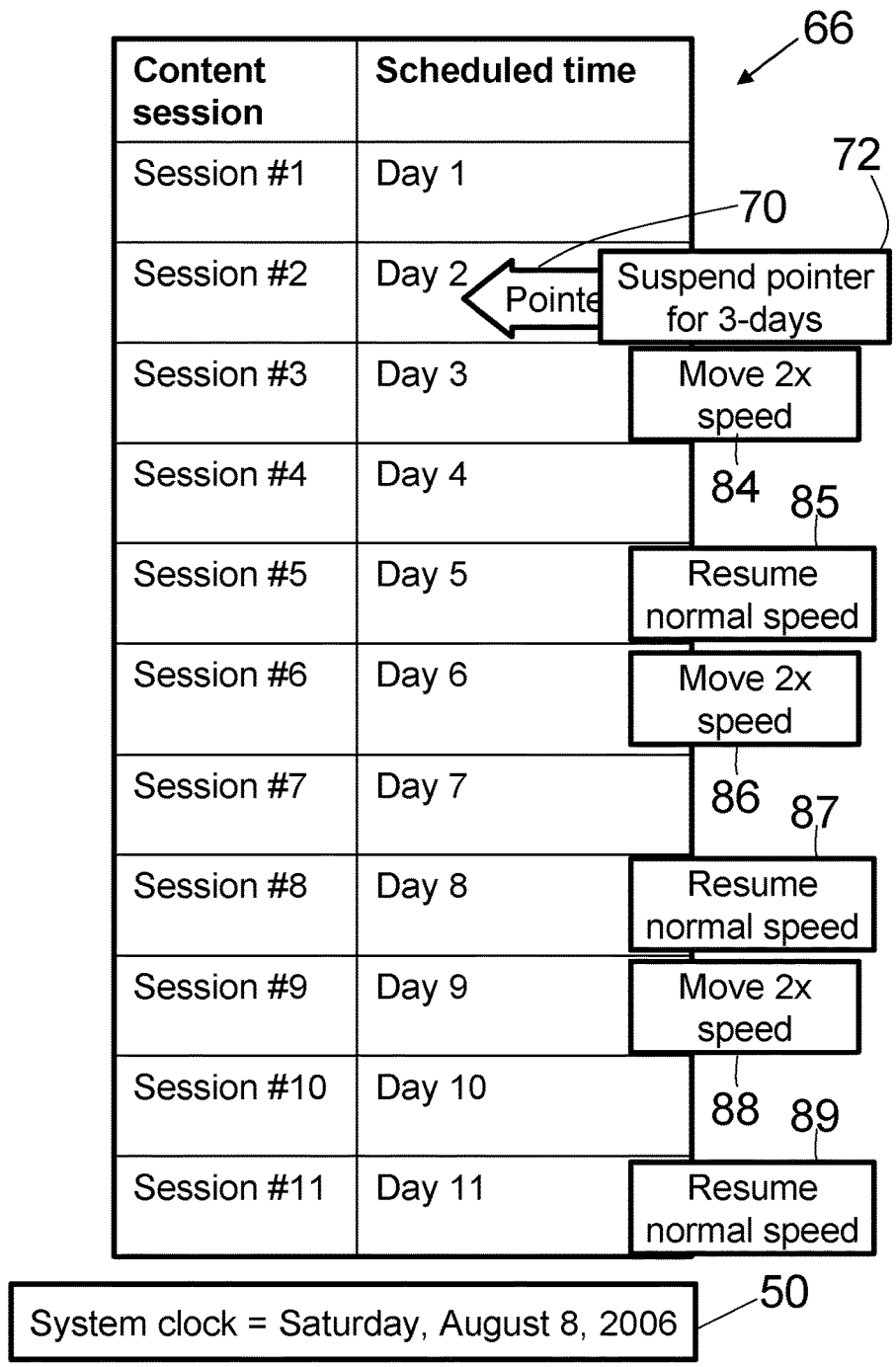
FIG. 10 diagrammatically shows operative adjustment of the initial relative-date schedule of FIG. 6 to free up the vacation by suspending movement of the schedule pointer during the vacation so as to free up the vacation period, and also speeds up the schedule subsequent to the vacation by speeding up movement of the schedule pointer in the time period proximate to but after the vacation.

With reference to FIG. 10, another approach can be used to generate a revised speeded-up relative-time schedule. The relative-time schedule 66 continues to be followed, but with the automatic schedule adjustments being operatively achieved by adjusting the movement of the schedule pointer 70. As in the automatic adjusting of FIG. 8, at Day 2 the instruction 72 is issued by the processor 26 to suspend temporal movement of the schedule pointer 70 for the selected three-day translation time interval. This frees up the three-day vacation 54. Upon resumption of movement of the schedule pointer 70 at Day 3, an instruction 84 is issued to increase movement speed of the schedule pointer 70 by a factor of two. In this way, both the Session #3 scheduled for Day 3 and the Session #4 scheduled for Day 4 are accomplished in real-time on the same day, namely on Saturday Aug. 12, 2006. On Day 5 which in real-time is now Sunday Aug. 13, 2006, an instruction 85 is issued to resume normal speed of the schedule pointer 70. Accordingly, on Day 5 corresponding to Sunday Aug. 13, 2006, only Session #5 is presented. On Day 6 corresponding to Monday Aug. 14, 2006, an instruction 86 is issued to increase movement speed by a factor of two. In this way, both the Session #6 scheduled for Day 6 and the Session #7 scheduled for Day 7 are accomplished in real-time on the same day, namely on Monday Aug. 14, 2006. On Day 8 which in real-time is now Tuesday Aug. 15, 2006, an instruction 87 is issued to resume normal speed of the schedule pointer 70. Accordingly, on Day 8 corresponding to Tuesday Aug. 15, 2006, only Session #8 is presented. On Day 9 corresponding to Wednesday Aug. 16, 2006, an instruction 88 is issued to increase movement speed by a factor of two. In this way, both the Session #9 scheduled for Day 9 and the Session #10 scheduled for Day 10 are accomplished in real-time on the same day, namely on Wednesday Aug. 16, 2006. On Day 11 which in real-time is now Thursday Aug. 17, 2006, an instruction 89 is issued to resume normal speed of the schedule pointer 70. Accordingly, on Day 11 corresponding to Thursday Aug.

17, 2006, only Session #11 is presented. Thereafter, the scheduling is back to the initial scheduling of FIG. 6, and so no further pointer movement adjustments are called for. It will be appreciated that this relative-date schedule processing produces the same real-time result as the revised absolute-date schedule 80 of FIG. 9.

With reference to FIG. 11, in another alternative revised absolute-date schedule 90 differs from the revised schedule 80 of FIG. 9 in that the session #3 is doubled-up with Session #2 on Tuesday, Aug. 8, 2006, which is proximate to but before the patient unavailability time period corresponding to the vacation 54. This approach is optionally used if the patient provides enough advance notice of the patient unavailability or other selected time period 54. In effect, a portion of the speeded-up scheduling is disposed temporally before the patient unavailability time period corresponding to the vacation 54, so that after the vacation 54 only two doubled-up days are needed (Sunday August 13 and Tuesday August 15 in the revised schedule 90 of FIG. 11) to get back onto the initial schedule after the vacation 54.

In the same way that the schedule can be speeded up, the schedule can also be slowed down, either by translating sessions or by changing the speed of the schedule pointer. A schedule slow-down may be desirable, for example, just before a vacation to taper off the patient's scheduled activities.

FIG. 12 depicts another alternative revised absolute-date schedule 100 constructed from the initial absolute-date schedule 56 of FIG. 4. The revised schedule 100 enables speeding up of the schedule portion proximate to but after the patient unavailability time period corresponding to the vacation 54. In the revised schedule 100, the Sessions #3, #4, and #5 which were previously scheduled coincident with the patient unavailability time period 54 are now omitted. To cover the a material of these content sessions, the Sessions #6, #7, and #8 which were previously scheduled subsequent to the patient unavailability time period 54 are replaced by modified Sessions #6', #7', and #8' which include make-up material corresponding to that of omitted Sessions #3, #4, and #5. This approach can be useful in that the modified Sessions #6', #7', and #8' may include the subject matter of the omitted Sessions #3, #4, and #5 in an abbreviated or concise manner, thus enabling the patient to catch up more quickly than by doubling-up sessions as in the revised schedule 80. However, implementing the schedule 100 calls for availability of the modified Sessions #6', #7', and #8' which include the additional material.

FIG. 13 depicts another alternative revised absolute-date schedule 110 constructed from the initial absolute-date schedule 56 of FIG. 4. The revised schedule 110 is similar to the revised schedule 56' of FIG. 5 that is constructed by applying a translational three-day revision to all scheduled content coincident with or subsequent to the patient unavailability time period corresponding to the vacation 54. The revised schedule 110 differs from the revised schedule 56' in two ways. First, a four-day translation is used, rather than a three-day translation. Thus, in the revised schedule 110, Session #3 is scheduled for presentation on Sunday, Aug. 13, 2006, Session #4 is scheduled for presentation on Monday, Aug. 14, 2006, and so forth. It will be appreciated that the four-day translation frees up both the three days of the vacation 54 (Wednesday August 9 through Friday August 11) and the first day after the vacation 54 (Saturday Aug. 12, 2006). The second difference between revised schedule 110 and revised schedule 56' is that Session #2 which was presented on Tuesday Aug. 8, 2006, that is, just before commencement of the vacation 54, is in the revised schedule 110 scheduled for re-presentation on Saturday Aug. 12, 2006. This approach of adjusting the schedule to re-present one or more sessions that were presented before commencement of the patient unavailability time period 54 can be useful in situations where the patient may need a refresher session. Rather than re-presenting an entire previously presented session, a different, shortened review session that summarizes the pre-vacation session may be presented after return from the vacation 54.

FIG. 14 depicts another alternative revised absolute-date schedule 120 constructed from the initial absolute-date schedule 56 of FIG. 4. The revised schedule 120 is similar to the revised schedule 56' of FIG. 5 that is constructed by applying a translational three-day revision to all scheduled content coincident with or subsequent to patient unavailability time period corresponding to the vacation 54. The revised schedule 120 differs from the revised schedule 56' in that on the first day after the vacation 54, that is on Saturday Aug. 12, 2006, an added content session 122, namely Session HS containing an interactive health survey, is presented. The health survey Session HS 122 is doubled-up with Session #3 on Saturday Aug. 12, 2006. The patient answers questions presented in Session HS 122, which may for example include an interactive quiz, survey, test, or questionnaire. The illustrated revised schedule 120 is tentative in that the scheduled presentation of Session #3 and subsequent sessions is conditional upon the survey answers indicating that the patient is in satisfactory condition. However, if the patient's answers to the health survey Session HS 122 are unsatisfactory (for example, indicating a substantial weight gain over the vacation 54, an injury sustained over the vacation 54, a demonstration of insufficient retention of previously covered material, or so forth), then an alternative revised subsequent schedule may be applied, such as inserting another session which suggests that the patient schedule a follow-up visit with the doctor, suggesting that the patient go back to Session #1 for review purposes, or starting a different series targeting a more pressing condition that developed during the vacation.

With reference to FIGS. 15 and 16, in some embodiments the content sessions are organized into modules, such as the illustrated Goal Module #1 and Goal Module #2 of FIG. 15. Goal Module #1 is constructed of the Sessions #1-#10 of the schedule of FIG. 4, while Goal Module #2 is constructed of different Sessions #A-#H. For example, the Goal Module #1 may be directed toward the goal of increasing patient exercise, while the Goal Module #2 may be directed toward a different goal such as teaching the patient to use a certain medical device. As shown in FIG. 15, the two goal modules are suitably independently scheduled. The initial schedule for Goal Module #1 is the same as that of FIG. 4, while an initial schedule 130 is constructed for Goal Module #2. Thus, for example, on Monday Aug. 7, 2006 the patient is presented with Session #1 from Goal Module #1 and Session #A is presented from Goal Module #2; on Tuesday Aug. 8, 2006 the patient is presented with Session #2 from Goal Module #1 and Session #B is presented from Goal Module #2; and so forth. Alternatively, the sessions of the two Goal Modules can be interleaved, e.g., presented on alternate days.

With reference to FIG. 16, each of the two schedules 56, 130 are suitably independently adjusted to achieve rescheduling that frees up the patient unavailability time period corresponding to the vacation 54. For example, as shown in FIG. 16, the schedule 56 is adjusted by a three-day time translation of the Sessions #3-#10 to produce the revised schedule 56' of FIG. 5 for Goal Module #1. In contrast, a revised schedule 130' is constructed for Goal Module #2 by speeding up the schedule 130 proximate to but outside of the vacation 54. Thus, the Session #C which was initially coincident with the vacation 54 is doubled up with Session #B on Tuesday, Aug. 8, 2006 just prior to the vacation 54. Sessions #D and #E also initially coincident with the vacation 54 are doubled-up on the first day after the vacation 54, that is, on Saturday August 12. Session #F which was initially scheduled for Saturday August 12 (proximate to but outside of the vacation 54) is assigned a new presentation date of Sunday August 13. Session #G which was initially scheduled for Sunday August 13 (proximate to but outside of the vacation 54) is assigned a new presentation date of Monday August 14, thus doubling-up with Session #H so that the revised schedule 130' for Goal Module #2 completes on the same day as the initial schedule 130 for Goal Module #2. The two Goal Modules may each be re-scheduled as suggested in one of the preceding embodiments or other patterns.

The rescheduling performed by the suitably configured processor 26, 44 can be performed multiple times. For example, the initial schedules of FIG. 15 may be automatically adjusted to produce the revised schedules of FIG. 16. Thereafter, if another period of patient unavailability arises, the schedules of FIG. 16 may be further automatically adjusted to produce a further revised schedule (not shown) that frees up the newly recognized period of patient unavailability. Moreover, while in the illustrated embodiments entire sessions are moved or suspended, it is also contemplated to move or suspend only portions of sessions. The selected time period that is freed up by the re-scheduling can be for something other than the illustrated example of a vacation or other patient unavailability time period. For example, the re-scheduling may be to free up a selected time period in which the patient is available but wants to engage in an activity that makes it difficult to follow the schedule. As another example, the re-scheduling may free up a selected time period in order to add or insert one or more additional sessions to the schedule at the selected time period. Such added or inserted sessions may relate to different goals than the original schedule, or may reinforce the goals of the original schedule.

It should be appreciated that all of the content need not be presented to the patient, such as in cases were the patient has extended suspended period. This can occur if the patient is on extended vacation or if the patient has a different health emergency that requires direct care for a prolonged period. In such cases, it is important for the patient to receive information on a prioritized basis such that the most important portions of the care plan are provided in a more expeditious manner. The following describes some implementations for prioritization of material which would allow the patient to obtain the most essential information first, thereby preventing the patient from being overwhelmed by a large amount of missed material.

In a most basic model, information or material can be flagged by the care plan designer or health care provider as "essential" or "non-essential". During the course of a normal plan care, all material (i.e. essential and non-essential) is provided to the patient in accordance with the care plan. If there has been an extended period in which the patient is unavailable for whatever reason and the care plan is suspended, upon resumption, the care plan can be restructured to only provide the essential material that would have been presented during the suspended period. The presentation of the material, or the order of the sessions to be completed, can occur in any manner (such as some of the methods discussed above) to allow the patient to comfortably get back into the care plan. This could mean presenting all of the missed essential material or sessions first, or, alternatively, presenting the missed essential material in combination with new material or sessions. In such embodiments, the non-essential material would not need to be presented. However, in some alternative embodiments, the timing of the presentation of the material is dictated by the essential or non-essential flag. In such cases, the essential material is presented on a prioritized time scale, whereas the non-essential material is presented, possibly selectively, later in the care plan once the patient has caught up to the current status of the prescribed care plan.

In a more advanced model, material or sessions can be flagged with a relative prioritization scale. The prioritization scale may be, for example, from 1 to 10, with 10 being the highest prioritization. In such cases, the material or sessions missed during a suspended period would be presented in order of the prioritization flags, such that the highest level of prioritization is presented first. The prioritization flags can be used also to intertwine the missed material with the new material. In some situations, it may be desirable to present only material with a certain level of prioritization. For example, a patient may only be deemed to need material that is flagged with a prioritization level of 5 or higher. The level of prioritization that is presented to the patient may depend on the particular patient, the goal module that the material or session is a part of, the type of care plan the material or session is apart of, the overall care plan type for the patient, a survey response provided by the patient, input from the patient's doctor or care provider, the length of time of the suspension, the amount of material or sessions that were missed, the criticality of the patient, or any combination of these factors. For example, a patient that has been on a care plan suspended a longer time may have a higher prioritization level (e.g. 7) than then prioritization level (e.g. 5) given to a patient who has had a care plan suspended for a shorter time period. In another example, a patient with a more severe diagnosis may have a lower prioritization (e.g. 4) than a patient with a less severe diagnosis (e.g. 7). Another factor that can determine the prioritization level may be the patient's acuity. For example, a patient with diminished capacity may have a higher prioritization level (e.g. 8) than a more normal patient (who may have a prioritization level of 5), based on the ability to review and retain material. A person with diminished capacity may become more overwhelmed if presented more material than absolutely required. The acuity level of the patient can be entered by the health care provider, tested throughout the course of the care plan, or tested upon resumption of the care plan.

Any of these prioritization schemes can also be applied within a specific session or material presentation. For example, a session may include a video clip that can be divided into five sections and then is followed by a quiz. In some situations, one or two sections of the video and the quiz may be deemed high priority or essential, while the remaining sections of video may be deemed low priority or non-essential. Upon resumption, the care plan may only include the sections of the session or material presentation that are deemed high priority or essential.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Have described the preferred embodiment, the invention is now claimed to be:

1. A method performed by a personalized interactive care management system, the method comprising:

using a server comprising a computer of the personalized interactive care management system, presenting content to a patient following a patient care plan provided for the patient wherein the content is divided into content sessions each comprising video, textual, survey, or questionnaire content, and the patient care plan specifies at least an order of presentation of the content sessions;

receiving notice at the server of a time period during which the patient is unavailable to receive presented content;

suspending the presenting of content to the patient following the patient care plan for the time period; and after the time period, resuming the presenting of content to the patient following the patient care plan wherein the order of presentation of the content sessions presented after the time period is rescheduled based on a prioritization scheme by which the content is prioritized and the content sessions presented after the time period include content sessions scheduled to be presented during the time period but not presented during the time period due to the suspending.

2. The method of claim 1, wherein the prioritization scheme includes prioritizing content sessions of the care plan as essential or non-essential and only content sessions prioritized as essential are presented after the time period.

3. The method of claim 1, wherein the prioritization scheme includes prioritizing content sessions of the care plan on a prioritization level and content with a higher prioritization level are presented first after the time period.

4. The method of claim 1, wherein the prioritization scheme depends upon a length of time of the time period during which the patient is unavailable to receive presented content.

5. The method of claim 1, wherein the content sessions are organized into goal modules with each goal module directed to a goal for the patient, and the prioritization scheme prioritizes content sessions based on the goal module that the content session is a part of.

6. The method of claim 1, wherein the prioritization scheme prioritizes content based on a survey response provided by the patient.

7. The method of claim 1, wherein the presenting of content includes presenting the content on a user interface.

8. The method of claim 1, wherein the presented content session comprises video content.

9. A method for managing care performed by a personalized interactive care management system, the method comprising:

using a server comprising a computer of the personalized interactive care management system to present content to a medical patient following a medical patient care plan provided for a medical patient wherein the content comprises video, textual, survey, or questionnaire content;

suspending the medical patient care plan for a time period wherein the suspending of the medical patient care plan comprises receiving notice at the server of a time period during which the medical patient will be unavailable to receive the presented content and suspending the presenting of content to the medical patient following the medical patient care plan for the time period; and after the time period, resuming the medical patient care plan based on a prioritization scheme that includes prioritizing portions of the care plan on a prioritization level that is based on the medical patient's capacity;

wherein upon the resumption of the medical patient care plan, only portions of the medical patient care plan with a predetermined prioritization level or higher are maintained in the medical patient care plan and presented after the time period.

10. The method of claim 9, wherein the medical patient's capacity is represented as an acuity level entered by a healthcare provider.

11. The method of claim 9, wherein the medical patient's capacity is represented as an acuity level tested upon resumption of the medical patient care plan.

12. A method for managing care performed by a personalized interactive care management system, the method comprising:

using a server comprising a computer of the personalized interactive care management system, maintaining patient care plans provided for respective patients wherein the content of each patient care plan is divided into content sessions each comprising video, textual, survey, or questionnaire content, and wherein each patient care plan specifies a schedule defining an order of presentation of the content sessions;

using the server, presenting content to patients following respective patient care plans;

receiving notice at the server of a time period during which a notifying patient is unavailable to receive presented content;

suspending the presenting of content to the notifying patient for the time period;

updating the patient care plan for the notifying patient by rescheduling the order of presentation of the content sessions to be presented after the time period based on a prioritization scheme by which the content is prioritized wherein the updating includes rescheduling content sessions scheduled to be presented during the time period but not presented during the time period due to the suspending to be presented after the time period; and after the time period, resuming the presenting of content to the notifying patient following the updated patient care plan for the notifying patient.

13. The method of claim 12 wherein the prioritization scheme includes prioritizing content sessions of the patient care plan for the notifying patient as essential or non-essential and the updating comprises retaining only content sessions prioritized as essential in the updated patient care plan for the notifying patient.

14. The method of claim 12 wherein:
the prioritization scheme includes prioritizing content sessions of the care plan on a prioritization level; and
the updating comprises ordering content with a higher prioritization level to be presented first upon resuming the presenting after the time period.

* * * * *